United States Patent [19]

Graves et al.

[11] Patent Number: 5,362,842
[45] Date of Patent: Nov. 8, 1994

[54] UREA-FORMALDEHYDE RESIN COMPOSITION AND METHOD OF MANUFACTURE THEREOF

[75] Inventors: Larry R. Graves, Puyallup; Jay V. Mueller, Tacoma, both of Wash.

[73] Assignee: Georgia Pacific Resins, Inc., Atlanta, Ga.

[21] Appl. No.: 118,760

[22] Filed: Sep. 10, 1993

[51] Int. Cl.$^5$ .............................................. C08G 12/12
[52] U.S. Cl. ................................... 528/262; 210/732; 210/764; 428/435; 428/228; 428/245; 528/242; 528/232; 528/261; 528/26
[58] Field of Search ............... 528/261, 262, 232, 242; 428/436; 210/732, 764

[56] References Cited

U.S. PATENT DOCUMENTS

| | | | |
|---|---|---|---|
| 2,260,033 | 10/1941 | Klenle et al. | 525/443 |
| 2,626,251 | 1/1953 | James et al. | 528/262 |
| 3,883,462 | 5/1975 | Pearson | 524/843 |
| 3,893,963 | 7/1975 | Sausaman | 524/843 |
| 3,976,465 | 8/1976 | O'Connell | 71/13 |
| 4,119,598 | 10/1978 | Pearson | 524/711 |
| 4,182,839 | 1/1980 | Tesson | 528/254 |
| 4,250,069 | 2/1981 | Yates | 524/843 |
| 4,370,442 | 1/1983 | Pearson | 524/598 |
| 4,482,699 | 11/1984 | Williams | 528/260 |
| 4,603,191 | 7/1986 | Kong | 528/259 |
| 4,663,239 | 5/1987 | Pearson | 428/524 |
| 4,735,972 | 4/1988 | Shigematsu | 523/102 |
| 4,968,773 | 11/1990 | Whiteside | 156/307 |
| 5,017,641 | 5/1991 | Kempter et al. | 524/598 |
| 5,034,500 | 7/1991 | Garrigue et al. | 528/259 |

FOREIGN PATENT DOCUMENTS

WO92/16461 1/1992 WIPO.

*Primary Examiner*—John Kight, III
*Assistant Examiner*—Terressa Mosley
*Attorney, Agent, or Firm*—Banner, Birch, McKie and Beckett

[57] ABSTRACT

A urea-formaldehyde resin useful as a binder for making a variety of products, and of a method for making the resin. The resin is prepared by reacting formaldehyde, urea, triethanolamine, and optionally ammonia in a two-step process, first under alkaline conditions and then under acidic conditions. The urea-formaldehyde resin thus produced has good resistance to hydrolysis, cures quickly without smoking, and is characterized by low formaldehyde release.

20 Claims, No Drawings

UREA-FORMALDEHYDE RESIN COMPOSITION AND METHOD OF MANUFACTURE THEREOF

BACKGROUND OF THE INVENTION

1. Field of the Invention

This invention relates to a urea-formaldehyde resin composition, to methods of manufacturing the resin and using it, and to products prepared using the resin. More particularly, the invention relates to a urea-formaldehyde resin composition which is resistant to hydrolysis, cures quickly without smoking, and exhibits low formaldehyde emission. The resin is useful as a binder for making glass fiber mats and metal acid salt briquettes or composites.

2. Description of Related Art

Often, products containing fibrous or particulate materials are manufactured by binding the materials together by use of a binding composition. Such compositions typically are known as "binders".

Binders not only retain the fibrous or particulate materials in the desired orientation or shape, but also impart physical characteristics to the product. For example, mats of glass fibers bound together have a variety of forms and uses, such as support sheets for vinyl and other types of composite flooring, roofing shingles, or siding. Various types of binders are also used in the art to maintain the physical integrity of ferrous sulfate briquettes used in, for example, deodorizing applications and in fashioning other types of composites.

Preferred characteristics of binders used to bind glass fibers may be different from preferred characteristics of binders used to bind particulates. For example, it may be desirable to utilize a binder that is soluble in a preselected solvent so that the bound material is released into that solvent. It may be desirable to make the binder freely soluble in some solvent, affording quick release of the bound material, or to make the binder only sparingly soluble, thus delaying release of the material. Because the characteristics exhibited by the binder contribute to the overall characteristics of the product, the binder must be carefully selected.

Unpleasant odors and toxic gases emanate from various daily living environments and various facilities such as cattle farms, poultry farms and sewage disposal plants. Such odors are caused by acidic malodorous gases, such as hydrogen sulfide, as well as alkaline malodorous gases, such as ammonia. Various compounds such as ferrous sulfate, aluminum sulfate, zinc sulfate, zirconium oxide, zirconium phosphate, and titanium oxide are known to remove the bad odors of ammonium. Zinc oxide, magnesium oxide, iron oxide and iron hydroxide, while not very good at removing gaseous ammonia, have been used to eliminate hydrogen sulfide.

U.S. Pat. No. 4,735,972 discloses the incorporation of ferrous sulfate, aluminum sulfate, potassium aluminate sulfate, sodium aluminum sulfate or zinc sulfate into a thermoplastic resins to form a composition having deodorizing properties which can be molded into articles, such as bag for garbage disposal.

Published PCT Application No. 92/16461 discloses blocks of solid material made with synthetic resins containing at least formaldehyde and ferrous sulfate. The blocks may be reinforced with, for example, wood chips or fibers, cellulose fibers, and or acid peat. Gases collect on and are held by the peat, causing the blocks to float. A urea-formaldehyde resin having a U:F molar ratio between 1:1.1 and 1:1.5 is disclosed for use. The blocks are placed in, for example, basins situated under animals in breeding areas and float on the animal sewage surface where the ferrous sulfate is liberated gradually from the block to neutralize free ammonia by forming ammonia-ferro-sulfate and partially deodorize the sewage.

Typical binders used to bind glass fiber mats include urea-formaldehyde resins, phenolic resins, bone glue, polyvinyl alcohols, and latexes. These binder materials are impregnated directly into the fibrous mat and set or cured to provide the desired integrity for the glass fibers. The most widely used binder is urea-formaldehyde because it is inexpensive.

Glass fibers also have been used by themselves and in combination with other types of fibers in the production of paper-like sheet materials. Glass fibers have been used as such a supplemental fiber in specialty, synthetic, fiberboard, pulp, and composite papers, and are finding a use in glass fiber paper, a substitute for papers made of asbestos fiber. Also, there has been and continues to be increasing use of a nonwoven, sheet-like mat of glass fibers (particularly chopped glass fibers or strands, and combinations thereof) as a replacement for organic felts such as cellulose mats in roofing shingles and buildup roofing systems (BUR systems).

Use of the glass fiber mats in the roofing industry provides several advantages. These advantages include: reduction in the amount of asphalt necessary for the roofing products, reduction in the weight of the roofing products, increased production rates for producing roofing products, superior rot resistance, longer product life, and improved fire ratings. These nonwoven, sheet-like mats usually are produced in a process in which glass fibers (chopped fibers, chopped fiber strands, strands, and combinations thereon are dispersed in an aqueous medium and formed into a mat. The nonwoven, sheet-like mat product is produced by contacting the mat of glass fibers with a polymeric binder. An example of such a process is the "wet-laid process". Descriptions of the wet-laid process may be found in a number of U.S. patents, including U.S. Pat. Nos. 2,906,660, 3,012,929, 3,050,427, 3,103,461, 3,228,825, 3,760,458, 3,766,003, 3,838,995 and 3,905,067, all of the teachings of which are incorporated herein by reference.

The wet-laid process involves forming, usually with agitation in a mixing tank, an aqueous slurry of glass fibers, typically chopped fibers or chopped strands of suitable length and diameter. Other forms of glass fibers, such as continuous strands, also may be used. Generally, fibers having a length of about inch to 3 inches and a diameter of about 3 to 20 microns are used. Each bundle may contain from about 20 to 300, or more, of such fibers, which may be sized or unsized, wet or dry, as long as they can be suitably dispersed in an aqueous dispersant-containing medium. The bundles are added to the medium to form an aqueous slurry. Any suitable dispersant known in the art, e.g., polyacrylamide, hydroxyethyl cellulose, ethoxylated amines, and amine oxides, may be used. The dispersant is employed in relatively small amounts, e.g. 0.2–10 parts in 10,000 parts of water.

The fiber slurry is agitated to form a workable, well-dispersed slurry having a suitable consistency. The aqueous slurry, often referred to as slush, is processed into the wet-laid, nonwoven, sheet-like mat by such machines as cylinder or Fourdrinier machines. More technologically-advanced machinery, such as the StevensFormer, RotoFormer, InverFormer, and the VertiFormer machines, also are used. The slush is deposited in some manner from a head box onto a moving wire screen or onto the surface of a moving wire-covered cylinder. On route to the screen, the dispersion usually is diluted with water to a lower fiber concentration. The slurry on the screen or cylinder is processed into the sheet-like that by the removal of water, usually by suction and/or vacuum devices, and the application of a polymeric binder. Binder composition is applied by soaking the mat in an excess of binder solution, or by coating the mat surface by means of a binder applicator, for example, by roller or spray. Suction devices often are utilized for further removal of water and excess binder and to ensure a thorough application of binder.

Thus-incorporated binder is cured, typically in an oven at elevated temperatures. Generally, a temperature of at least about 200° C. is used during curing. Normally, this heat treatment alone will effect curing. Catalytic curing, such as is accomplished with an acid catalyst (for example, ammonium chloride or p-toluene sulfonic acid), generally is a less desirable alternative.

Typically, when urea-formaldehyde resins are used as a binder component they release formaldehyde into the environment during cure or formaldehyde is released from the cured resin, particularly when the cured resin is exposed to acidic environments. Such release is undesirable, particularly in enclosed atmospheric environments. In such environments, formaldehyde is inhaled and comes into contact with the eyes, the mouth, and other parts of the body. Formaldehyde is malodorous and causes human and animal illness.

Various techniques have been utilized to reduce formaldehyde release from urea-formaldehyde resins. Use of formaldehyde scavenger and various methods for resin formulation, including addition of urea as a reactant late in the resin formation reaction, are techniques used to reduce formaldehyde emission. However, use of formaldehyde scavenger often is undesirable, not only because of the additional cost, but also because it affects the characteristics, or properties, of the resin. For example, using ammonia as formaldehyde scavenger reduces the resistance of the cured polymer to hydrolysis (degradation). Later addition of urea to reduce free formaldehyde concentration in the resin may yield a resin that must be cured at a relatively low rate to avoid smoking and polymer stability also can be adversely effected.

U.S. Pat. No. 2,260,033 describes a method which purportedly reduces the amount of free formaldehyde in a urea-formaldehyde resin. In the disclosed process, triethanolamine is added to a mixture of urea and formaldehyde having a 1:1 to 1.5:1 formaldehyde to urea mole ratio in an amount sufficient to neutralize its pH. The mixture is then reacted at 30° C. The resin is used to make molded objects, laminated material and films.

U.S. Pat. No. 2,626,251 describes the preparation of a water soluble, cationic urea-formaldehyde resin. The resin is disclosed as having a high degree of water resistance when cured and is suggested for use in textile applications and for adding wet strength to paper. The preferred resin is prepared by initially reacting urea and formaldehyde at a formaldehyde to urea mole ratio of at least 2.0 but less than 3.0 together with triethanolamine in a urea to triethanolamine mole ratio of 2.0 to not more than 3.0. The resin thus-formed then is made cationic by acidifying it to a pH below 2.5, and preferably at least 1.5, with a strong inorganic acid such as hydrochloric, sulfuric or nitric, followed by prompt neutralization to a pH of 6 to 7. A pH above 7 is discouraged as this is said to retard the cure of the resin.

U.S. Pat. No. 3,882,462 to Pearson, describes a urea-formaldehyde resin prepared by reacting sequentially aqueous formaldehyde, a catalyzing acid, triethanolamine and urea. The aqueous resin is taught for use in coatings, adhesives and textile finishes. The preferred resin is prepared using 30 moles of formaldehyde, 2 moles of acid, preferably phosphoric acid, 2 moles of triethanolamine and 12 moles of urea. The various reactants are said to react, without applied heat, as rapidly as the materials are mixed together. In U.S. Pat. No. 4,119,598, said to be an improvement on the '462 patent, the formaldehyde, urea and triethanolamine are mixed before addition of the acid and the molar quantities, based on about 30 moles of formaldehyde, are changed to 0.13 mole acid, 1.6 mole triethanolamine and 9.9 moles urea. In yet another improvement patent, U.S. Pat. No. 4,370,442, melamine is included in the reaction mix to expand the resin's water dilutability and storage stability. Finally, in U.S. Pat. No. 4,663,239, Pearson describes including ammonium hydroxide, ammonium chloride and ammonium formate in the composition to reduce formaldehyde emissions.

U.S. Pat. No. 4,492,699 describes a urea-formaldehyde resin adhesive for wood composites, such as particle board, characterized by slow formaldehyde emission. The patent indicates that by increasing the level of methylene linkages in the resin. instead of dimethylene ether linkages and methylol end groups, hydrolytic degradation, which contributes to increased formaldehyde emission, is reduced. To accomplish this goal, the resin is prepared in a process having two stages of condensation and two stages of methylolation. In a first condensation stage, urea is added to a highly acidic formaldehyde solution (pH of 0.5 to 2.5) at a formaldehyde to urea mole ratio of 2.5 to 4.0. The initial stage is very exothermic and proceeds without the application of heat. The reaction can be controlled to a temperature in the range of 50° C. to 99° C. by adding the urea incrementally. Thereafter, the resin solution is neutralized and additional urea is added. Triethanolamine is one of several bases mentioned for neutralizing the resin and a combination of sodium hydroxide and triethanolamine is preferred. After the second stage, the formaldehyde to urea mole ratio is within the range of 1.5: 1.0 to 2.5: 1.0. The second step is conducted at a temperature of 50° C. to 80° C. to permit methylolation to proceed slowly. The resin then is switched again to an acidic pH, heated to reflux and reacted to a desired viscosity. Finally, the resin is neutralized to slight alkalinity (pH of 7.3-7.5) and additional urea is added to provide a cumulative formaldehyde to urea mole ratio of 1.1:1.0 to 2.3:1.0. Methylolation is said to thereafter proceed during storage. Thereafter, the resin is cured to an infusible state during use by adding ammonium chloride and heating at 115° C. for 15 minutes.

U.S. Pat. No. 4,968,773 describes preparing a urea-formaldehyde resin purportedly having a low extractable formaldehyde content by first methylolating urea under alkaline conditions (pH of 6-11) at a formaldehyde to urea mole ratio within the range of 2:1 to 3:1, followed by condensation at a low (acid) pH (pH of 0.5-3.5), then neutralizing the resin (pH of 6.5-9) and adding additional urea to yield a final formaldehyde to urea mole ratio of 1.8:1 or less.

SUMMARY OF THE INVENTION

This invention is based on the discovery of a urea-formaldehyde resin and of a method for making the resin. The resin is prepared by reacting formaldehyde and urea, a minor amount of triethanolamine, and optionally ammonia in a particular two-step process.

In the first reaction step, the reactant mixture containing formaldehyde, urea, triethanolamine and optionally ammonia is reacted at an alkaline pH and heated. The reaction mixture is held at an elevated temperature for a time sufficient to ensure complete methylolation of the urea.

In the second reaction step, an acid is added to the reaction mixture in an amount sufficient to reduce the pH to less than 7 and reaction is continued under acidic conditions. Additional urea is then added and the reaction is continued. A plurality of urea addition/reaction steps are utilized until the formaldehyde to urea mole ratio is reduced to a desired level. The resin then is cooled and neutralized.

The urea-formaldehyde resin thus produced has good resistance to hydrolysis, cures quickly without smoking, and is characterized by low formaldehyde release. The resin is useful as a binder polymer for wet chopped glass fibers, where low formaldehyde release is a desired property for the working environment. It has also been unexpectedly discovered that the resin can be used as a low formaldehyde-emitting binder polymer for metal salts, such as ferrous sulfate, in the preparation of briquettes, where low formaldehyde release also is a requirement.

DETAILED DESCRIPTION OF THE INVENTION

The invention is based on the discovery of a process which uses a small amount of triethanolamine as a modifier for urea-formaldehyde polymers as a means of reducing free formaldehyde while not sacrificing speed of polymer cure and cured polymer resistance to hydrolysis. In particular, it has been discovered that the use of triethanolamine as a modifier, particularly in conjunction with ammonia, imparts improved control of formaldehyde emissions from urea-formaldehyde polymers even when exposed to acidic environments. The resin is prepared by reacting formaldehyde (F), urea (U), triethanolamine (TEA), and optionally ammonia in a two-step process.

In the first reaction step, formaldehyde, urea, triethanolamine and optionally ammonia are charged into a reaction vessel. The reactants can be introduced into the reactor in any convenient manner or order. The quantity of each reactant added to the reactor is that quantity sufficient to achieve molar F/U/TEA/ammonia ratios in the range (1.50:4.0):1:(0.001–0.1):(0-.0–0.5). Each reactant can be introduced in one charge or in a plurality of charges. It is preferred that the quantities of each reactant be sufficient to maintain a F/U/TEA/ammonia molar ratio within the range of (1.50–4.0):1:(0.001–0.1 ):(0.0–0.5) during the first reaction step.

The pH of the reactant mixture is maintained above about 7, preferably above about 8, measured at the reaction temperature at the beginning of the reaction. During the course of the first reaction step, the pH typically stays above about 7. The alkaline reaction mixture is heated to a temperature of at least about 70°, preferably above about 80° C. most preferably to a temperature of about 95° C. Generally, the reaction mixture is heated to a temperature of about 95° C. over a period of about 30 minutes. The reaction mixture is held at the elevated temperature for a time sufficient to ensure complete methylolation of the urea in a controlled time frame. Generally, 15 to 20 minutes at about 95° C. is sufficient.

In the second reaction step, a mineral or organic acid is added to the reaction mixture in a quantity sufficient to achieve an acidic pH condition in the reactant mass, a pH of about 5 being preferred. The acid can be added in a single charge, or in a plurality of charges. Reaction then is continued under this acid condition at an elevated temperature, typically above about 75° C., for a time sufficient to reduce free formaldehyde to less than 2%, preferably less than 1%, generally for about 45 to 240 minutes, preferably for about 90 to 120 minutes. A reaction temperature of about 95° C. for about two hours is suitable. Depending on the initial F:U molar ratio, further urea additions and reaction periods are repeated until the F/U mole ratio is reduced to between about 1.5:1 and 2.5:1. It is important to maintain the pH at about 5 at the time of any such additional urea additions to obtain desired resin properties. For example, after the initial second reaction step, the reaction mixture is then cooled, for example, to about 80° C. and additional urea is added and reaction is continued for about one additional hour. A plurality of urea addition/reaction steps can be utilized until the desired final F/U mole ratio is reached.

Additional triethanolamine then can be added, if desired. The resin then is cooled to ambient conditions and can be neutralized, for example, by the addition of sodium hydroxide to quench the reaction.

Skilled practitioners recognize that the reactants are commercially available in many forms. Any form which can react with the other reactants and which does not introduce extraneous moieties deleterious to the desired reaction and reaction product can be used in the preparation of the urea-formaldehyde resin of the invention.

Formaldehyde is available in many forms. Paraform (solid, polymerized formaldehyde) and formalin solutions (aqueous solutions of formaldehyde. often with methanol, in 37 percent, 44 percent, or 50 percent formaldehyde concentration) are commonly used forms. Formaldehyde also is available as a gas. Any of these forms is suitable for use in the practice of the invention. Typically, formalin solutions are preferred as the formaldehyde source.

Similarly, urea is available in many forms. Solid urea, such as prill, and urea solutions, typically aqueous solutions, are commonly available. Further, urea may be combined with another moiety, most typically formaldehyde and urea-formaldehyde, often in aqueous solution. Any form of urea or urea in combination with formaldehyde is suitable for use in the practice of the invention. Both urea prill and combined urea-formaldehyde products are preferred.

TEA typically is supplied as a liquid, often combined with diethanolamine and monoethanolamine. Although any form of TEA is suitable for use in the claimed method and product, it is preferred to use TEA products having only minimal diethanolamine and monoethanolamine contaminants. Preferably, the TEA weight concentration is at least about 10 times the sum of the diethanolamine and monoethanolamine weight concentrations, and more preferably is about 20 times that sum.

Skilled practitioners recognize that ammonia is available in various gaseous and liquid forms, including particularly aqueous solutions at various concentration. Any of these forms is suitable for use. However, commercially-available aqueous ammonia-containing solutions are preferred herein. Such solutions typically contain between about 10 and 35 percent ammonia. Aqueous solution containing about 28 percent ammonia is particularly preferred.

Use of ammonia and/or late additions of urea are commonly used prior art techniques to reduce free formaldehyde levels in urea-formaldehyde polymer systems. The former technique suffers from reducing the cured polymers resistance to hydrolysis. The latter technique suffers from a tendency to produce a polymer system that releases smoke during the cure cycle. This invention suffers from neither of these problems, but significantly reduces free formaldehyde levels during cure and in the cured product.

The use of a scavenger changes the state of the formaldehyde from free formaldehyde to a pH unstable monomer that decomposes with time under acidic conditions to release formaldehyde. It has been discovered that the polymer of the present invention is more pH stable and releases significantly less formaldehyde than a polymer synthesized without the presence of the minor modifying amount of triethanolamine when exposed to acidic environments. This attribute makes the resin particularly useful as a binder for metal salts, particularly metal acid salts, in the preparation of briquettes for use in deodorizing animal sewage, since such products are exposed to acidic hydrogen sulfide emanating from waste materials.

The resin of the invention also is advantageously used in the preparation of glass fiber mats to be used, for example, in the manufacture of roofing shingles. For example, glass fibers are slurried into an aqueous dispersant medium. The glass slurry is then dewatered on a foraminated surface to form a mat. The binder resin of the invention is then applied to the mat before it passes through a drying oven where the mat is dried and the incorporated binder resin is cured. Glass fiber mats so-produced with the resin of this invention exhibit low formaldehyde emission and exhibit good dry and hot wet tensile strength, as well as good tear strength.

Binder compositions made with the resin of the present invention can also be used as a binder for composites containing metal acid salts. The binder can be incorporated directly with the metal salt with subsequent mechanical mixing, or in an aqueous form by being sprayed thereon and subsequently mixed therein. Known extrusion and/or compaction techniques also can be used to form pellets, blocks or briquettes. Curing proceeds at ambient temperature due to the presence of the acid salt. The binder can be incorporated with the metal salt in an amount of from about 3 % to about 30% by weight binder solids per weight of the salt, with about 10 to 12% being preferred.

In addition to ferrous salts such as ferrous sulfate, examples of other metal salts useful in the invention include ferric, zinc, aluminum, zirconium, copper salts and combinations thereof. Copper sulfate is especially useful for preparing briquettes for use in algae control.

In the invention, which will now be described in more specific terms, a quantity of urea and formaldehyde and, if desired, fresh water, in an amount to provide an initial formaldehyde to urea molar ratio of between about 1.50 and 4.0, preferably 2.75 to 4.0, are charged into a stainless steel reactor equipped with agitator. TEA then is added in a minor amount to provide a TEA to urea mole ratio of between 0.001:1 to 0.10:1, the reactants mixed and pH recorded. The pH preferably should be between about 8.0 and about 8.4. more preferably about 8.2.

In the preferred practice of the invention, ammonium hydroxide is then charged into the reactor in an amount to provide an ammonia to urea ratio of about 0.2:1.0 to 0.5:1.0. The ammonium hydroxide is added as quickly as possible, preferably in 25 minutes or less.

Under normal conditions, the addition of the ammonium hydroxide will cause the temperature of the reactant mass to exotherm to 70°–75° C. The temperature is then maintained at a minimum temperature of 75° C. and held at 75–80° C. for a minimum of 5 minutes. During this 5 minute hold, the pH is checked. A pH of between about 7.8 and 8.5 is desirable. If the solution is above 8.5, it is adjusted downwardly to the desired range with 7.0% sulfuric acid.

The temperature is then cooled to below about 70° C., preferably below about 45° C. With the temperature at or below 50° C., the urea is added as rapidly as possible to bring the reactant mixture within the aforementioned molar ratio range. The addition of urea will cause the reaction mixture to endotherm and assist in this cooling.

Starting at about 40° C., the reaction mixture is heated to about 95° C. over the course of 30 minutes. The exotherm of the reaction will assist in the upheat. Heating can be controlled with vacuum and/or with cooling coils. During the upheat cycle the pH will drop. It is very important that pH be monitored at least every 10 minutes during the upheat cycle. The reaction mixture is held at 95° C. for 15 to 20 minutes during which time the pH should level off to between about 6.8 and 7.3. If the pH drops too low, the pH during the acid condensation step will be lower and the resin will advance more rapidly. In order to control resin advancement, the pH can be raised by the addition of alkaline or, alternatively, reaction temperature can be decreased.

A 7.0% sulfuric acid solution thereafter is added over a 10 minute period. Addition of sulfuric acid must be made beneath the resin surface in an area of mixing such that dispersion is very rapid and no gelled particles are formed. Over the next hour, the pH of the reactant mass will drop to about 4.9 to about 5.2. If the pH is allowed to level off above 5.2, resin advancement will be retarded. Thus, additional small amounts of 7.0% sulfuric acid may be needed to bring the pH into the desired 4.9 to 5.2 range. Caution, however, must be used if the pH drops below 4.9, since the rate of resin enhancement will increase rapidly as the pH is lowered. If the pH drops below 4.9, aqueous 25–50 % sodium hydroxide can be used to raise the pH into the 4.9–5.2 range or the temperature can be lowered, for example, to 90° C. or lower, to maintain control of resin advancement. Upon reaching the desired viscosity, the reactants are cooled to 80° C., which will slow the rate of viscosity advancement. More urea then is added to reduce the cumulative F:U mole ratio to the desired level and the reactant mass is reacted for 40–60 minutes at 80° C. to maintain an adequate advancement rate. If the rate of advancement slows, the temperature should be increased. It is not necessary, or even desirably, to add more acid to lower the pH. At this stage, only temperature generally should be used to control the rate of advancement. An increase of 5° C. will double the rate of advancement. A decrease of 5° C. will cut the rate of advancement. The temperature, however, normally should not be allowed to drop below 78° C. during resin advancement.

It is to be understood that a single urea addition in the second reaction stage, as illustrated herein, may be sufficient to obtain the desired mole ratio and resin properties. Two, three or even four or more loads of urea may, however also be used. The number of urea additions, and the amount of urea added, will depend on the desired resin properties, including formaldehyde to urea mole ratio, viscosity, desired solubility and cure rate, and will be readily determinable by one skilled in the art using routine experimentation within the parameters taught herein. Additional charges of TEA can also be used. Additional modifiers, such as melamine, ethylene ureas and dyaniamide can also be incorporated into the resin of the invention. Finally, further urea additions for purposes of scavenging formaldehyde or as a diluent also may be used.

The following examples are for purposes of illustration and are not intended to limit the scope of the claimed invention.

EXAMPLE 1

The following reactants were used to prepare a urea-formaldehyde resin.

|  | g |
|---|---|
| UFC 85 | 2334.7 |
| formalin solution, 50% CH$_2$O | 200.3 |
| fresh water | 113.8 |
| TEA, 85% (first charge) | 16.0 |
| NH$_4$OH, 28% | 512.3 |
| urea (first charge) | 256.1 |
| H$_2$SO$_4$, 7% | 135 |
| urea (second charge) | 470.6 |
| TEA #2 (second charge) | 8.7 |

A resin was prepared by charging UFC 85 (25% urea, 60% formaldehyde and 15% water), formalin and fresh water into a reactor and heated with agitation to 40° C. TEA and NH$_4$OH were then added and held for 5 minutes. The first urea charge was added with continued cooling at 40° C. The reaction mixture was then heated to 95° C. over the course of 30 minutes and held at 95° C. for 15 minutes. The pH was monitored and adjusted to 5.0 to 5.3 by the addition of from 10 to 25 g of H$_2$SO$_4$. A total of 135 g being added over the course of one hour. The reaction mixture was cooled to 80° C. The second urea charge was added over the course of 5 minutes, heated to 85° C. and maintained at this temperature for a period of one hour after which the second charge of TEA was added and the temperature cooled to 25° C. pH was adjusted to a pH of 7.4–7.6 using a 5.5 g of 25% NaOH. The initial amount of formaldehyde was decreased from 3.60 moles to 2.30 moles per mole of urea in the final product. The amount of ammonia being 0.40 mole per mole of urea. The fresh free formaldehyde level was 0.12% at 0° C. After 24 hours free formaldehyde levels were 0.0%. Free formaldehyde levels were run using the sodium sulfite ice method.

EXAMPLE 2

Glass fiber mats were prepared by adding 0.50 g of surfactant (Katapol VP-532), 0.50 g of defoamer (Nalco 2343) and 6.50 g OCF 685 1"-M cut glass fibers obtained from Owens Corning Fiberglass to 7.50 liters of polyacrylamide containing white water having a viscosity of 3.0 cps and mixed for 3 minutes. Excess water was drained and then vacuum dewatered on a formaminated surface to form a wet glass fiber mat. The urea-formaldehyde binder prepared in accordance with Example 1 was applied on the fiber mat and excess binder removed by vacuum. The mat was then placed in a Werner Mathis oven for 60 seconds at 205° C. to cure the resin.

Ten cut samples were tested for tensile strength under dry conditions and after soaking in an 82° C. water bath for 10 minutes on an Instron with a crosshead speed of 2 inches and a jaw span of 3 inches. Tear strength was tested on cut samples using an Elmendorf Tear Machine. The mean results are shown in Table 1, with standard deviations being shown in parentheses.

TABLE 1

| | | | TEST RESULTS OF MAT MADE WITH 1" - M OCF 685 | | | | | | | |
|---|---|---|---|---|---|---|---|---|---|---|
| | | | DRY TENSILE TESTS | | | MD WET TENSILE TEST | | | TEAR | |
| Roll No. | Mat Wt. | LOI % | MD | CMD | square MD/C MD | Dry | Wet | W/D | MD | CMD | Total |
| GP 314T21 (Control Resin) | | | | | | | | | | | |
| — | 1.88 | 22 | 141 (17.1) | 107 (9.1) | 1.32 | 132 | 70 | 0.53 | 376 (39) | 454 (136) | 830 |
| GP 346T80 (Resin of the Invention) | | | | | | | | | | | |
| 5 | 1.83 | 24 | 121 (7.3) | 100 (14.6) | 1.21 | 130 | 72 | 0.55 | 324 (27) | 410 (38) | 734 |
| 6 | 1.84 | 19 | 117 (6.2) | 95 (3.8) | 1.23 | — | — | — | — | — | — |
| 7 | 1.90 | 18 | 145 (6.7) | 101 (9.0) | 1.44 | 125 | 65 | 0.52 | 330 (29) | 418 (78) | 748 |
| 8 | 1.89 | 21 | 120 (5.5) | 90 (8.7) | 1.33 | — | — | — | — | — | — |
| 9 | 1.82 | 20 | 133 (10.2) | 111 (8.3) | 1.20 | 114 | 68 | 0.60 | 294 (23) | 330 (8) | 624 |
| 10 | 1.90 | 23 | 140 (10.2) | 100 (8.3) | 1.40 | — | — | — | — | — | — |
| 11 | 1.90 | 21 | 133 (12.4) | 115 (10.7) | 1.16 | 130 | 73 | 0.56 | 358 (37) | 396 (30) | 754 |
| 12 | 1.93 | 21 | 153 (7.7) | 117 (6.5) | 1.31 | — | — | — | — | — | — |
| 13 | 1.86 | 20 | 144 (13.4) | 109 (4.9) | 1.32 | 116 | 65 | 0.56 | 316 (24) | 384 (30) | 700 |
| 14 | 1.96 | 20 | 134 (15.0) | 98 (21.9) | 1.37 | — | — | — | — | — | — |
| 15 | 1.84 | 20 | 141 (11.7) | 104 (6.8) | 1.36 | 124 | 67 | 0.54 | 364 (46) | 394 (34) | 758 |
| 16 | 1.86 | 21 | 123 (8.3) | 94 (5.3) | 1.31 | — | — | — | 390 (24) | 424 (60) | 814 |
| 17 | 1.76 | 17 | 120 (3.6) | 99 (7.9) | 1.21 | 109 | 64 | 0.59 | 374 (30) | 386 (20) | 760 |
| 18 | 1.86 | 18 | 142 (9.3) | 111 (5.9) | 1.28 | — | — | — | — | — | — |
| *19 | 1.94 | 18 | 123 (11.0) | 101 (1.7) | 1.22 | 111 | 60 | 0.54 | 408 (31) | 522 (30) | 930 |

EXAMPLE 3

The following reactants were used to prepare a urea-formaldehyde resin.

| | g |
|---|---|
| UFC 85 | 1004.6 |
| formalin solution, 50% CH$_2$O | 1767.6 |

-continued

|  | g |
| --- | --- |
| fresh water | 22.1 |
| TEA | 18.7 |
| NH4OH, 28% | 367.1 |
| urea (first charge) | 686.3 |
| H2SO4, 7% | 83.6 |
| urea (second charge) | 311.3 |
| NaOH, 25% | 11.0 |
| urea (third charge) | 155.9 |
| urea (fourth charge) | 73.8 |

A resin was prepared by charging UFC 85, formalin and fresh water into a reactor and heated with agitation to 45° C. TEA and NH4OH are added and held for 5 minutes. The reaction was then cooled to 50° C. and the first urea charge added. The reaction mixture was then heated to 95° C. over the course of 30 minutes and held at 95° C. for 15 minutes, pH was monitored and adjusted to 5.1 by the addition of sulfuric acid. The reaction mixture was cooled to 85° C. and the second urea charge was added over the course of 5 minutes. The pH was adjusted to 7.0-7.4 by the addition of NaOH. A third urea charge was added and held for 20 minutes to scavenge free formaldehyde. The reaction medium was cooled to 40° C. A fourth charge of urea was made and the resin cooled to 25° C.

The ammonia to urea ratio was 0.30. The formaldehyde to urea ratio went from 3.00 following the first urea charge, to 2.25 following the second urea charge, to 2.00 following the third charge of urea, to 1.90 following the fourth charge. Fresh free formaldehyde level was 0.69%. Twenty-four hour free-formaldehyde levels were <0.5 ppm. Free formaldehyde levels were determined using the sodium sulfite ice method

EXAMPLE 4

140 g of FeSO4 was mixed with 25.2 g urea-formaldehyde resin of Example 3 of the invention and 2.3 g of peat and compressed under pressure. Due to the presence of the acid salt, curing of the resin occurs at ambient temperature. Using this laboratory prepared mix, without additional water, as a binder for ferrous sulfate briquettes, the mixture became stiff to firm in 15 minutes.

Small amounts of water can be added, about 7% based on the ferrous sulfate, if desired, to increase the pot life of the mix. If additional pot life is needed, polymer formulation can be modified to adjust the setting cycle of the polymer.

We claim:

1. A method of preparing a urea-formaldehyde resin comprising:

mixing formaldehyde, urea, triethanolamine and optionally ammonia reactants at an alkaline pH, heating the mixture to an elevated temperature for a time sufficient to obtain complete metholylation of the urea, the reactants being present in an amount of about 1.50 to 4.0 moles of formaldehyde, about 0.001 to 0.1 mole of triethanolamine, and about 0.0 to 0.5 mole ammonia, per mole of urea, and adding acid to lower the pH to within the range of about 4.9 to about 5.2 and adding urea until the molar formaldehyde to urea ratio is within the range of about 1.5:1 to about 2.5:1 and reacting for a time sufficient to reduce free formaldehyde to less than 2%.

2. The method of claim 1 wherein the reaction mixture of formaldehyde, urea, triethanolamine and ammonia is heated to a temperature of about 95° C. over a period of 30 minutes and maintained at a temperature of 95° C. for 15 to 20 minutes.

3. The method of claim 1 wherein the acid is a mineral acid.

4. The method of claim 1 wherein further additions of urea are added following addition of the acid.

5. The method of claim 1 wherein the formaldehyde, urea, triethanolamine and ammonia are mixed at a pH of about 8.0 to about 8.4.

6. A urea-formaldehyde resin prepared by a method comprising:

mixing formaldehyde, urea, triethanolamine and optionally ammonia reactants at an alkaline pH, heating the mixture to an elevated temperature for a time sufficient to obtain complete metholylation of the urea, the reactants being present in an amount of about 1.50 to 4.0 moles of formaldehyde, about 0.001 to 0.1 mole of triethanolamine, and about 0.0 to 0.5 mole ammonia, per mole of urea, and adding acid to lower the pH to within the range of about 4.9 to about 5.2 and adding urea until the molar formaldehyde to urea ratio is within the range of about 1.5:1 to about 2.5:1 and reacting for a time sufficient to reduce free formaldehyde to less than 2%.

7. The resin of claim 6 wherein the reaction mixture of formaldehyde, urea, triethanolamine and ammonia is heated to a temperature of about 95° C. over a period of 30 minutes and maintained at a temperature of 95° C. for 15 to 20 minutes.

8. The resin of claim 6 wherein a mineral acid is used to lower the pH.

9. The resin of claim 6 wherein further additions of urea are added following addition of the mineral acid.

10. The resin of claim 6 wherein the formaldehyde, urea, triethanolamine and ammonia are mixed at a pH of about 8.0 to about 8.4.

11. The resin of claim 6 having a molar formaldehyde to urea ratio of from about 1.5:1 to about 2.5:1.

12. A glass fiber mat made with the resin of claim 6.

13. A method of making a glass fiber mat using the resin of claim 6.

14. A metal salt briquette made with the resin of claim 6.

15. The briquette of claim 14 containing at least one metal salt selected from the group consisting of ferrous salts, ferric salts, zinc salts, aluminum salts, zirconium salts, and copper salts.

16. The briquette of claim 15 containing ferrous sulfate.

17. The briquette of claim 15 containing copper sulfate.

18. A method of making a metal salt briquette using the resin of claim 6.

19. A method of deodorizing a malodorous liquid comprising placing at least one briquette of claim 14 in said liquid.

20. A method of controlling algae in water comprising placing at least one briquette of claim 14 in said liquid.

* * * * *